(12) United States Patent
Chung et al.

(10) Patent No.: US 12,391,694 B2
(45) Date of Patent: Aug. 19, 2025

(54) PROCESS FOR THE PREPARATION OF 2-FLUOROADENINE

(71) Applicant: Merck Sharp & Dohme LLC, Rahway, NJ (US)

(72) Inventors: John Y. L. Chung, Edison, NJ (US); Cynthia Marilyn Hong, Harrison, NJ (US); Guy R. Humphrey, Hillsborough, NJ (US); Kevin M. Maloney, Metuchen, NJ (US); Yingju Xu, Edison, NJ (US); Richard J. Varsolona, Scotch Plains, NJ (US)

(73) Assignee: Merck Sharp & Dohme LLC

( * ) Notice: Subject to any disclaimer, the term of this patent is extended or adjusted under 35 U.S.C. 154(b) by 895 days.

(21) Appl. No.: 17/618,687

(22) PCT Filed: Jun. 18, 2020

(86) PCT No.: PCT/US2020/038304
§ 371 (c)(1),
(2) Date: Dec. 13, 2021

(87) PCT Pub. No.: WO2020/263660
PCT Pub. Date: Dec. 30, 2020

(65) Prior Publication Data
US 2022/0242866 A1 Aug. 4, 2022

Related U.S. Application Data

(60) Provisional application No. 62/865,610, filed on Jun. 24, 2019.

(51) Int. Cl.
*C07D 473/40* (2006.01)

(52) U.S. Cl.
CPC ............................ *C07D 473/40* (2013.01)

(58) Field of Classification Search
CPC ................................................. C07D 473/40
See application file for complete search history.

(56) References Cited

U.S. PATENT DOCUMENTS

| 5,180,824 | A | 1/1993 | Bauman et al. | |
|---|---|---|---|---|
| 7,339,053 | B2 | 3/2008 | Kohgo et al. | |
| 7,625,877 | B2 | 12/2009 | Kohgo et al. | |
| 8,202,991 | B2 | 6/2012 | Saischek | |
| 8,350,091 | B2 | 1/2013 | Hagiya et al. | |
| 2011/0092491 | A1* | 4/2011 | Cheng | C07D 473/34 514/263.22 |
| 2019/0022115 | A1 | 1/2019 | Girijavallabhan et al. | |
| 2019/0038631 | A1* | 2/2019 | Biggadike | C07D 473/16 |

FOREIGN PATENT DOCUMENTS

| CN | 105130989 A | 10/2017 |
|---|---|---|
| CN | 105130989 B | 10/2017 |
| WO | 2020014041 A1 | 1/2020 |

OTHER PUBLICATIONS

Hayashi. Pot economy and one-pot synthesis, Chemical Science, Nov. 2015, pp. 866-880. (Year: 2015).*
Sudhindra et al. Versatility of KF as Selective Fluorination of Organic Compounds for Halogen Exchange Reactions, Bhavnagar University, 2003, pp. 13-26. (Year: 2003).*
Allen et al. Developing Eï¬cient Nucleophilic Fluorination Methods and Application to Substituted Picolinate Esters, OPRD, Aug. 2014, pp. 1045-1054 (Year: 2014).*
Allen, Laura J. et al., Developing Efficient Nucleophilic Fluorination Methods and Applications to Substituted Picolinate Esters, Organic Process Research & Development, 2014, 1045-1054, 18.
Fukuyama, K., et al, "Synthesis of EFdA via a Diastereoselective Aldol Reaction of a Protected 3-Keto Furanose", Organic Letters, 2015, pp. 828-831, vol. 17, No. 4.
Hattori, S., et al, "Potent Activity of a Nucleoside Reverse Transcriptase Inhibitor", Antimicrobial Agents and Chemotherapy, 2009, pp. 3887-3893, vol. 53.
Hayashi, Yujiro, Pot economy and one-pot synthesis, Chemical Science, 2016, 866-880, 7.
Hu, Yu Lin et al., Synthesis and Biological Activity of Novel 6-Substituted Purine Derivatives, Journal of Mexican Chemical Society, 2010, 74-78, 54.
Kageyama, M., et al, "Enantioselective Total Synthesis of the Potent Anti-HIV Nucleoside EFdA", Organic Letters, 2011, pp. 5264-5266, vol. 13, No. 19.
Kawamoto, A., et al, "2'-Deoxy-4'-C-Ethynyl-2-Halo-Adenosines Active Against Drug-Resistant Human Immunodeficiency Virus 1 Variants", Interational Journal of Biochemistry Cell Biology, 2008, pp. 2410-2420, vol. 40, No. 11.
Konstantinova, I.D. et al., The Arsenolysis Reaction in the Biotechnological Method of Synthesis of Modified Purine Beta-D-Arabinonucleosides, Russian Journal of Bioorganic Chemistry, 2016, 372-380, 42.

(Continued)

*Primary Examiner* — Sarah Pihonak
*Assistant Examiner* — Mikhail O'Donnel Robinson
(74) *Attorney, Agent, or Firm* — Eric Greenwald; John C. Todaro

(57) ABSTRACT

The present invention provides processes for the preparation of 2-fluoroadenine, as well as certain intermediates useful in the preparation of 2'-deoxy-4'-C-ethynyl-2-fluoroadenosine (EFdA): EFdA.

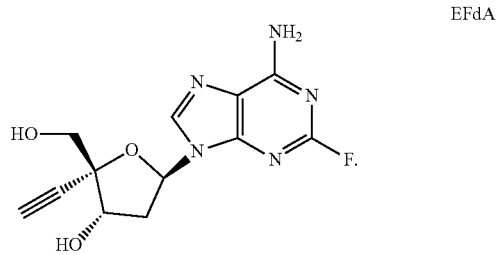

10 Claims, No Drawings

(56) References Cited

OTHER PUBLICATIONS

Montgomery, John A. et al., Synthesis of Potential Anticancer Agents. XX. 2-Fluoropurines, J. Am. Chem. Soc., 1960, 463-468, 82.
Ohrui, H., et al, 2'-Deoxy-4'-C-Ethynyl-2-Fluoroadenosine: A Nucleoside, Nucleosides, Nucleotides & Nucleic Acids, 2007, pp. 1543-1546, vol. 26.
PubChem CID 21856103 Create Date: Dec. 5, 2007 (Dec. 5, 2007), p. 2, entire document (10 pages).
PubChem CID 4595415 Create Date: Sep. 16, 2005 (Sep. 16, 2005), p. 2, entire document (7 pages).

* cited by examiner

PROCESS FOR THE PREPARATION OF 2-FLUOROADENINE

BACKGROUND OF THE INVENTION

4'-Ethynyl-2'-fluoro-2'-deoxyadenosine (EFdA) is a nucleoside reverse transcriptase translocation inhibitor that blocks HIV-1 and SIV viral replication in vitro (Kawamoto, A., Kodama, E., Sarafianos S. F. et al, *Int. J. Biochem. Cell Biol.*; 40 (11):2410-20 [2008]; Ohrui, H., Kohgo, S., Hayakawa, H. et al, *Nucleosides, Nucleotides & Nucleic Acids*, 26, 1543-1546 [2007]) and in vivo (Hattori, S., Ide, K., Nakata, H. et al. *Antimicrobial. Agents and Chemotherapy*, 53, 3887-3893 [2009]). EFdA is claimed in U.S. Pat. No. 7,339,053 (referred to in the '053 patent as 2'-deoxy-4'-C-ethynyl-2-fluoroadenosine). EFdA has the following chemical structure:

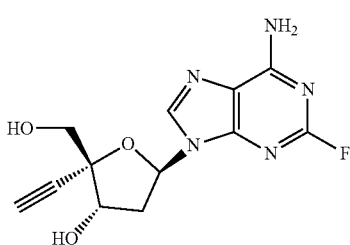

EFdA

Published preparations of EFdA utilize the nucleobase, 2-fluoroadenine, as a key synthetic intermediate in glycosylation coupling reaction with various modified ribofuranosyl intermediates. Several routes to EFdA have appeared in the scientific literature, including two reports in Organic Letters published in 2011 and 2015 (Kuwahara et al., *Org. Lett.* 2011, 13, 5264 and Kuwahara/Ohrui et al., *Org. Lett.* 2015, 17, 828). Both of these literature routes utilize a glycosylation involving a modified, acetylene-bearing ribosyl intermediate and 2-fluoroadenine. More recently, U.S. Patent Application Publication No. 2019-0022115-A1 discloses a process for the preparation of 4'-ethynyl-2'-deoxyribonucleosides, which uses 2-fluoroadenine to couple with an acetylene-bearing ribosyl intermediate to prepare EFdA. International Application Publication No. WO 2020/014041, published Jan. 16, 2020 discloses an enzymatic synthesis EFdA which involves a glycosylation of an ethynyl-bearing 2-deoxyribose intermediate with 2-fluoroadenine catalyzed by the enzyme purine nucleoside phosphorylase.

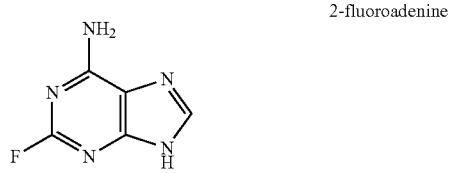 [SMILES: Nc1nc(F)nc2[nH]cnc12]

2-fluoroadenine

Several preparations of 2-fluoroadenine are known the published literature. For instance, Montgomery et al. in *J. Am. Chem. Soc.*, 82, 463 (1960), discloses the preparation of 2-fluoroadenine from 2,6-diaminopurine and also from 2,6-diamino-9-benzylpurine. U.S. Pat. No. 5,180,824 discloses the preparation of 2-fluoroadenine by reduction of 6-azido-2-fluoropurine by either a dithiol-amine mixture or by sodium borohydride. China Patent No. CN 105130989B discloses the preparation of 2-fluoroadenine in two steps from 6-chloro-2-nitro-9-tetrahydropyranylpurine involving treatment with ammonium fluoride followed by methanolic ammonia.

The published routes to 2-fluoroadenine suffer drawbacks when producing multi-kilogram quantities of the intermediate which are required to prepare larger quantities of drug substance required for advanced clinical studies. For instance, the published routes to the intermediate produce crude products which require laborious work-up conditions, provide only low yields of the intermediate, or utilize reagents or reaction conditions that are unsuitable for scaled up preparations.

SUMMARY OF THE INVENTION

The present invention provides a process for the preparation of 2-fluoroadenine, which is a useful synthetic intermediate used in preparing antiviral nucleoside agents such as EFdA. In addition, the invention provides certain synthetic intermediates which are useful in preparing 2-fluoroadenine.

DETAILED DESCRIPTION OF THE INVENTION

In a first aspect, the present invention provides a process for preparing compound (4)

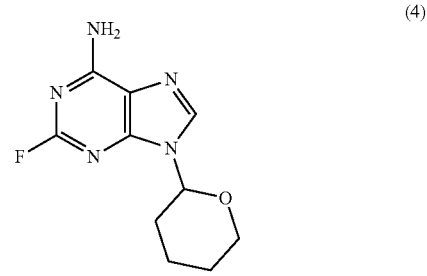 [SMILES: Nc1nc(F)nc2c1ncn2C1CCCCO1]

(4)

comprising:

(a) treating compound (2)

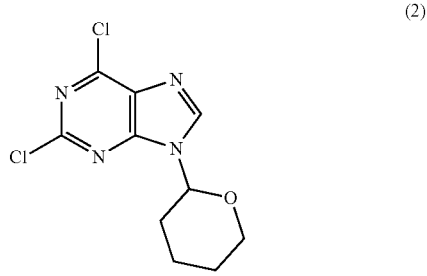 [SMILES: Clc1nc(Cl)c2ncn(C3CCCCO3)c2n1]

(2)

with a substituted amine reagent and a fluoride salt to provide compound (3); and

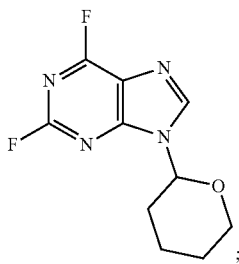

(3)

(b) treating compound (3) with an ammonia reagent to provide compound (4).

In a related, second aspect, the present invention provides a process for preparing 2-fluoroadenine

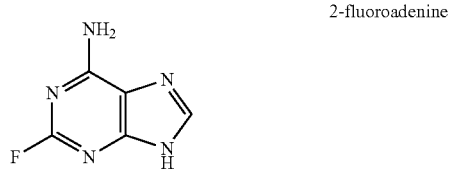 [SMILES: Nc1nc(F)nc2[nH]cnc12]

2-fluoroadenine comprising steps (a) and (b) of the process set forth above for the first aspect and step (c), which comprises treating compound (4) with an acid to provide 2-fluoroadenine.

In a related, third aspect, the present invention provides a process for preparing 4'-ethynyl-2-fluoro-2'-deoxyadenosine (EFdA)

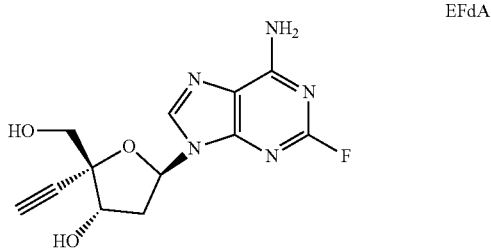 [SMILES: C#C[C@]1(CO)O[C@@H](n2cnc3c(N)nc(F)nc32)C[C@@H]1O]

EFdA comprising steps (a) and (b) of the process set forth above for the first aspect and step (c), which is converting compound (4) to EFdA.

In embodiment no. 1 of these processes, steps (a) and (b) are conducted in a single vessel. In this embodiment, the intermediate (3)

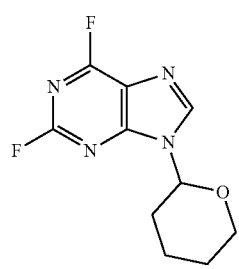

(3)

is not isolated before treatment with the ammonia reagent to yield compound (4)

Alternatively, in embodiment no. 2, the processes include isolating the intermediate compound (3) before treatment with the ammonia reagent to yield compound (4).

In embodiment no. 3 of these processes, the substituted amine reagent in step (a) is trimethylamine, dimethyl ethylamine, N-methylpyrrolidine, 1,4-diazabicyclo[2.2.2]octane (DABCO), tetramethylethylenediamine (TMEDA), or quinuclidine. In embodiment no. 4, the substituted amine reagent is trimethylamine.

In embodiment no. 5 of these processes, the fluoride salt in step (a) can be an alkali metal fluoride or a $C_1$-$C_4$ trialkylammonium fluoride (e.g., tetrabutylammonium fluoride). In embodiment no. 6, the fluoride salt is an alkali metal fluoride, for example, lithium, sodium, cesium, or potassium fluoride. In embodiment no. 7 of these processes, the fluoride salt is potassium fluoride. Typically, the fluoride salt is employed in molar excess as compared to the purine, such as from 2.0 to 10 molar equivalents, and preferably from 3 to 7 molar equivalents.

In certain preparations of embodiment no. 7, the potassium fluoride salt used has a surface area of 0.3 $m^2$/g or greater, for instance, in a range of 0.4-1.0 $m^2$/g.

In embodiment no. 8 of these processes, the ammonia reagent in step (b) is ammonia, aqueous ammonia (i.e., ammonium hydroxide), ammonia dissolved in an organic solvent (e.g., methanol, tetrahydrofuran), ammonium acetate, or ammonium carbonate.

In embodiment no. 9 of these processes, steps (a) and (b) are conducted in a dipolar aprotic solvent. For instance, in embodiment no. 10, steps (a) and (b) are performed in a dipolar aprotic solvent selected from dimethyl formamide, dimethylacetamide, dimethylsulfoxide (DMSO), acetonitrile or tetrahydrofuran. In some embodiments the dipolar aprotic solvent is dimethyl formamide. In other embodiments, the dipolar aprotic solvent is dimethylacetamide. In some embodiments, the concentration of the purine in the solvent is from 5-20 volumes.

In embodiment no. 11, the processes include the step of preparing compound (2) by reacting compound (1)

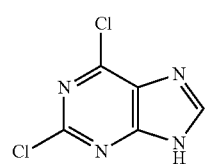

(1)

with dihydropyran in the presence of an acid to provide compound (2). The acid can be, for example, paratoluenesulfonic acid, trifluoroacetic acid, methanesulfonic acid and anhydrous acid resins. In embodiment no. 12, the acid is trifluoroacetic acid. The acid is typically added in a catalytic amount, such as from 0.01 to 0.1 molar equivalents as compared to the purine. The dihydropyran is typically employed in molar excess as compared to the purine, such as from 1.5 to 5 molar equivalents, and preferably from 2 to 4 molar equivalents.

In embodiment no. 13, step (c) of the second aspect comprises treating compound (4) with an acid to provide 2-fluoroadenine with an acid selected from a mineral acid, paratoluenesulfonic acid, or methanesulfonic acid. For example, in embodiment no. 14, the acid is phosphoric acid, sulfuric acid, hydrochloric acid para-toluenesulfonic acid, or methanesulfonic acid. The deprotection step is typically conducted with from 0.01 to 2 molar equivalents, e.g., 0.05 molar equivalents, as compared to the protected purine (4). Typically, this treatment is conducted in water, or a mixture of water with a water-miscible organic solvent, such as acetonitrile, at a temperature of 40 to 80° C.

In embodiment no. 14, step (c) of the third aspect compound (4) is converted to EFdA by treating compound (4) with an acid to provide 2-fluoroadenine, such as described in any one of embodiment nos. 11 or 12, and coupling the purine to a modified sugar moiety to form EFdA. For instance, in embodiment no. 15, 2-fluoroadenine can by enzymatically coupled with ammonium ((2R,3S)-2-ethynyl-3,5-dihydroxytetrahydrofuran-2-yl)methyl hydrogen phosphate (9) in a buffered solutions containing sucrose to provide EFdA. For instance, International Application Publication No. WO 2020/014041, published Jan. 16, 2020, which is herein incorporated by reference in its entirety, discloses catalysis of the coupling step with an enzyme solution containing phosphomutase and purine nucleoside phosphorylase.

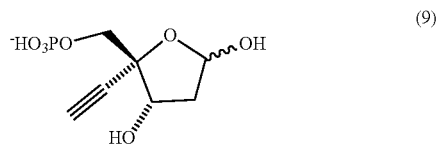

(9)

In embodiment no. 16, 2-fluoroadenine is coupled with the protected sugars as disclosed in U.S. Patent Application Publication No. US-2019-0022115-A1, followed by deprotection of the protected nucleoside intermediates to provide EFdA. For instance, 2-fluoroadenine can be coupled with (2R,3S)-5-acetoxy-2-ethynyl-2-(((4-methylbenzoyl)oxy) methyl)tetrahydrofuran-3-yl 4-methylbenzoate (10) or (2R, 3S)-2-ethynyl-2-[4-methylbenzoyl)oxymethyl]-5-(pent-4-en-1-yloxy)tetrahydrofuran-3-yl 4-methylbenzoate (11) as disclosed in Examples 3 and 4 of US-2019-0022115-A1, which examples are herein incorporated by reference.

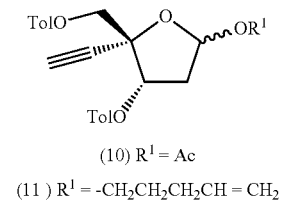

(10) R$^1$ = Ac
(11) R$^1$ = -CH$_2$CH$_2$CH$_2$CH = CH$_2$

Similarly, 2-fluoroadenine can be reacted with the protected sugar (12)

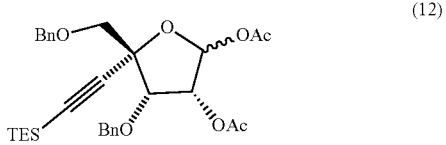

(12)

as disclosed in K. Fukuyama et al, *Org. Lett.* 2015, 17, 828-831, and further elaborated to EFdA.

In a fourth aspect, the present invention provides a process for preparing (3) comprising treating THP-protected 6-chloro-2-fluoropurine (8)

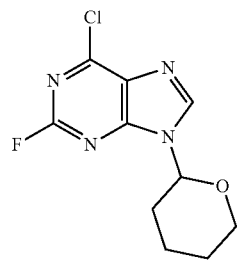

(8)

with a fluoride salt in an organic solvent selected from acetonitrile, α,α,α-trifluorotoluene, dimethylformamide, dimethylacetamide, tetrahydrofuran, or DMSO. For example in embodiment no. 17, compound (8) is treated with an alkali metal fluoride salt, e.g., cesium fluoride, in α,α,α-trifluorotoluene at a temperature of 70 to 100° C., e.g., 80° C. to provide (3).

In a fifth aspect, the present invention provides the compound (3)

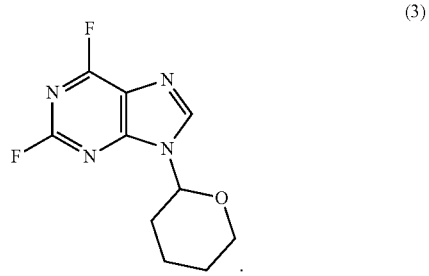 [SMILES: Fc1nc(F)c2ncn(C3CCCCO3)c2n1]

(3)

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

The term "alkyl," as used herein, refers to an aliphatic hydrocarbon group having one of its hydrogen atoms replaced with a bond having the specified number of carbon atoms. In different embodiments, an alkyl group contains from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

The term "ammonia agent," as used herein, refers to an ammonia- or ammonium-salt containing reagent capable of nucleophilic displacement of an aryl leaving group, e.g., a halo, to provide an amino-substituted aryl. Suitable examples of ammonia reagents include ammonia per se, aqueous ammonia (i.e., ammonium hydroxide), ammonia dissolved in an organic solvent (e.g., methanol, tetrahydrofuran), ammonium acetate, or ammonium carbonate.

The term "dipolar aprotic solvent, as used herein refers to a solvent with a high relative dielectric constant and a sizable permanent dipole moment, that cannot donate suitably labile hydrogen atoms to form strong hydrogen bonds. Examples of dipolar aprotic solvents include dimethyl sulfoxide, dimethyl formamide, dimethylacetamide, acetonitrile and tetrahydrofuran.

The term "halo," as used herein, means —F, —Cl, —Br or —I.

The term "high surface area potassium fluoride," as used herein, means potassium fluoride having a surface area of 0.3 $m^2/g$ or greater as determined by the Brunauer-Emmett-Teller (BET) method.

The term "mineral acid," as used herein, means common inorganic acids, such as hydrochloric acid, sulfuric acid, or nitric acid.

The terms "volume" or "volumes" when expressed in the context of specifying a numerical concentration of a compound, e.g., a reagent, in a solvent, as used herein, indicate the volume of solvent in mL per gram of reagent, or the volume of solvent in L per kg of reagent.

It should also be noted that any carbon as well as heteroatom with unsatisfied valences in the text, schemes, examples and tables herein is assumed to have the sufficient number of hydrogen atom(s) to satisfy the valences.

The compounds disclosed herein may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

All stereoisomers (for example, geometric isomers, optical isomers and the like) of the present compounds (including those of the salts and solvates of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC 1974 Recommendations*.

Compounds disclosed herein can, in certain instances, form salts which are also within the scope of this invention. Reference to a specific compound or synthetic intermediate useful for its preparation herein is understood to include reference to salts thereof, unless otherwise indicated. The term "salt(s)", as employed herein, denotes acidic salts formed with inorganic and/or organic acids, as well as basic salts formed with inorganic and/or organic bases.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), 1-hydroxy-2-naphthoates (also known as xinafoates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes the compounds disclosed herein in all their isolated forms. For example, the above-identified compounds are intended to encompass all forms of the compounds such as, any solvates, hydrates, stereoisomers, and tautomers thereof.

As used herein, the term "composition" is intended to encompass a product comprising the specified ingredients in the specified amounts, as well as any product which results, directly or indirectly, from combination of the specified ingredients in the specified amounts.

Abbreviations and acronyms employed herein include the following:

Ac—acetyl
18-Crown-6 = 1,4,7,10,13,16-hexaoxacyclooctadecane
DHP = 3,4-dihydro-2H-pyran
DMF = dimethylformamide
L = liter
LDA = lithium diisopropylamide
Me = methyl, Et = Ethyl, Pr = propyl, Bu = Butyl, Bz = benzoyl
MeOH = methanol
mL or ml = milliliter
mol = moles; M = molar
mmol = millimoles
MTBE—methyl tert-butyl ether
NMR = nuclear magnetic resonance
pet. ether = petroleum ether
Ppm, ppm = parts per million
pTSA = 4-toluenesulfonic acid
RBF = round bottomed flask
rt. = room temperature -continued TBAF = tetrabutylammonium fluoride
TFA = trifluoroacetic acid
THF = tetrahydrofuran
THP = tetrahydropyranyl
TLC = thin layer chromatography
TMS = trimethysilyl
Tol = p-methylbenzoyl General Chemical Procedures: All reagents were either purchased from common commercial sources or synthesized according to literature procedures beginning from commercial reagents. Commercial reagents were used without further purification. Certain starting materials can be prepared according to procedures known in the art. For example, 2,6-dichloropurine can be synthesized from xanthine via dichlorination chemistry (*J. Org. Chem.* 2011, 76, 4149-4153), or from 2-chloro-6-amino-purine via the Sandmeyer reaction (U.S. application Publication No. 2003/144508; *Journal of Heterocyclic Chemistry;* 48; 2011; 1140-1144; *European Journal of Medicinal Chemistry;* 126; 2017; 675-686; *Nucleosides, Nucleotides and Nucleic Acids;* 30; 2011; 503-511). 6-Chloro-2-fluoropurine can be prepared by the method disclosed in J. A. Montgomery et al. *J. Am. Chem. Soc.* (1960), 82, 463-468.

Nuclear magnetic resonance (NMR) spectra were recorded for $^1$H NMR at 500 MHz. Chemical shifts were reported in ppm relative to the residual deuterated solvent for $^1$H. Splitting patterns for $^1$H NMR signals are designated as: s (singlet), d (doublet), t (triplet), q (quartet), quint (quintuplet), broad singlet (br s) or m (multiplet). NMR spectra for $^{13}$C NMR were recorded at 126 MHz. NMR spectra for $^{19}$F NMR were recorded at 471 MHz.

The following scheme and examples are provided so that the invention may be more fully understood. These examples are illustrative only and should not be construed as limiting the invention in any way.

Scheme 1 shows one embodiment of the process of the present invention, wherein 2-fluoroadenine (2-FA) is prepared. As compared to prior-disclosed preparations of 2-fluoroadenine, the present processes is an efficient and green process, providing a defluorination reaction under very mild and non-acidic conditions, in contrast to acid reagents such hydrofluoric acid or hydrofluoboric acid. It also provides a highly selective amination to form (4). Crystalline intermediates (2) and (4) can be obtained with direct isolation without any extractive workup. While not being bound by any specific theory, the tetrahydropyranyl group of intermediate (3) is believed to stabilize the compound which avoids polymerization. A catalytic amount of acid in water with compound (4) quantitively releases 2-fluoroadenine.

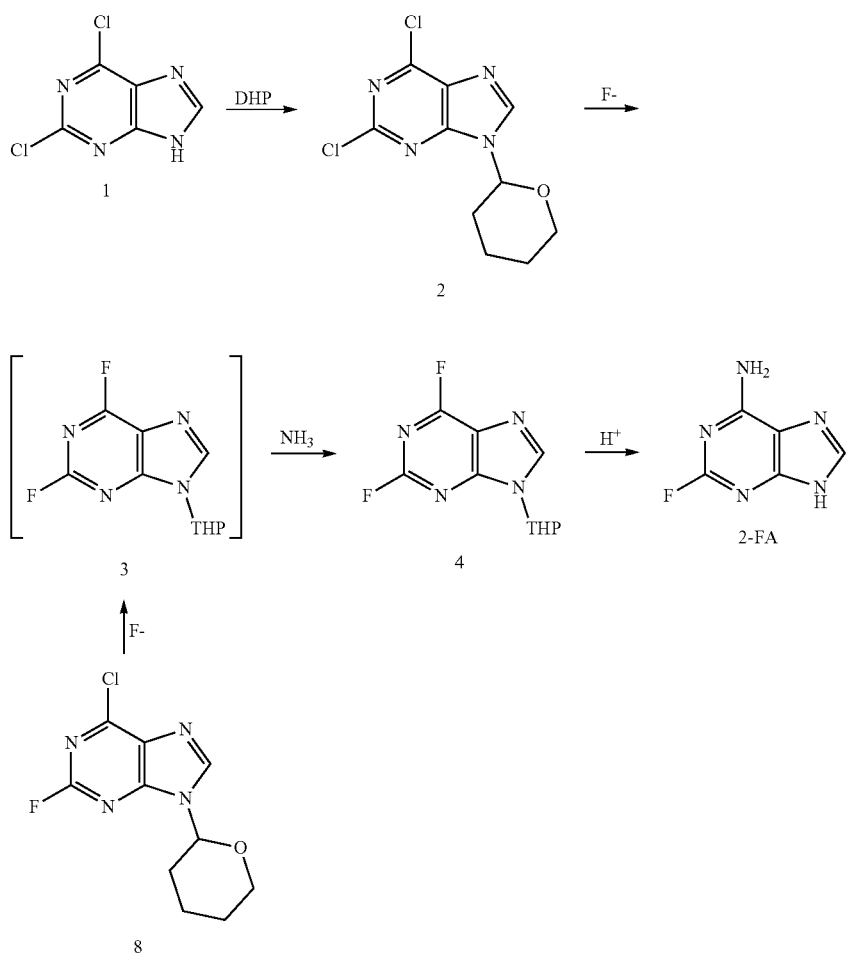

Scheme 1

As shown in Scheme 1, 2,6-dichloro-9H-purine (1) is treated with dihydropyran under acidic conditions to provide the protected dichloropurine intermediate (2). Treatment of intermediate (2) with a substituted amine reagent, e.g., trimethylamine and a fluoride salt provides the difluoropurine intermediate (3). Intermediate (3) may be isolated, but conveniently it can be carried on by treatment with ammonia, e.g., in a one-pot operation, to provide the protected 2-fluoroadenine intermediate (4). Applicants have observed that using anhydrous potassium fluoride with a surface area higher than 0.3 m$^2$/g is advantageous in the conversion of intermediate (3) to intermediate (4). By using high surface area potassium fluoride, fewer equivalents of the reagent are needed (e.g., 2.5 equivalents or less) needed to provide similar conversions and isolated yield as preparations using more equivalents of lower surface area potassium fluoride (e.g., 5 equivalents). In addition, in some embodiments it is advantageous to introduce seed crystals of compound (4) during work-up of the reaction to control purity and particle size of the isolated product.

Treating intermediate (4) with acid provides 2-fluoroadenine. Intermediate (3) may also be prepared by treatment of the protected 6-chloro-2-fluoro-9(H)-purine compound (8) with a fluoride salt.

EXAMPLES

Preparative Example

Preparation of High Surface Area Potassium Fluoride

Two lots of high surface area potassium fluoride were prepared, lot nos. 1 and 2. The duration of certain charging, distillation, and drying procedure different between the two lots as specified below. Both lots were useful in providing anhydrous, high-surface area potassium fluoride.

To vessel-1 was charged anhydrous potassium fluoride (12.0 kg) and MeOH (168 L, 14 V/kg). The batch was agitated for a few hours at 20° C. to 30° C. until a solution was formed. To vessel-2 was charged DMF (120 L, 10 V/kg) and the batch was agitated at 20° C. to 30° C. To vessel-2 was then charged the potassium fluoride solution in MeOH from vessel-1 over 0.2-24 hours (lot no. 1: 0.5 h; lot no. 2: 4 h). The mixture in vessel-2 was then concentrated to about 144 L (12 V/kg) with an internal temperature below 30° C. (lot no. 1: over 4 hours; lot no. 2: over 8 hours). The slurry was then filtered and the solid was slurry-washed with DMF (36 L, 3 V/kg) and 2×MTBE (36 L, 3 V/kg). The solid was then dried at 25° C. for 16 hours (lot no. 1) or with an extended drying at 50° C. for 24 hours (lot no. 2).

Result: Lot no. 1: yielded 10.8 kg potassium fluoride with a surface area of 0.88 m$^2$/g and 1.3% water content; Lot no. 2: yielded 11.0 kg potassium fluoride with a surface area of 0.70 m$^2$/g and 0.9% water content.

Example 1

Preparation of 2-Fluoro-9H-purin-6-amine (2-Fluoroadenine)

Step 1: Synthesis of 2,6-Dichloro-9-(tetrahydro-2H-pyran-2-yl)-9H-purine (2)

Three alternative preparations for preparing compound (2) were used.

Alternative A Into a 100 mL vessel was charged compound (1) (8 g, 42.3 mmol), ethyl acetate (8 mL) and 3,4-dihydro-2H-pyran (7.72 mL, 85 mmol). The white slurry was stirred at 23° C. and TFA (0.196 mL, 2.54 mmol) was charged. The reaction was stirred at 30° C. overnight and it became an almost clear solution. The reaction mixture was then concentrated and solvent switched to heptane at 30° C. The resulting slurry was then filtered and the solid was collected. The wet cake was washed with heptane three times and then dried under reduced pressure. Compound (2) was obtained in >95% isolated yield.

Compound (2): $^1$H NMR (500 MHz, DMSO-d$_6$) δ 8.93 (s, 1H), 5.74 (dd, J=10.7, 2.0 Hz, 1H), 4.01 (m, 1H), 3.74 (m, 1H), 2.26 (m, 1H), 1.99 (m, 2H), 1.76 (m, 1H), 1.59 (m, 2H). $^{13}$C NMR (126 MHz, DMSO-d$_6$) δ 153.22, 151.72, 150.42, 146.89, 131.08, 82.16, 68.22, 30.17, 24.86, 22.50.

Alternative B In a 2 L round bottom flask, 2,6-dichloro-9H-purine (1) (50 g, 265 mmol) was slurried in ethyl acetate (1000 mL). 3,4-Dihydro-2H-pyran (66.8 g, 794 mmol) was added followed by pTSA (0.911 g, 5.3 mmol). The reaction mixture was stirred at 50° C. for 1 hour and then cooled to room temperature. The mixture was transferred to a separatory funnel, washed with 10% aqueous NaHCO$_3$ solution (300 mL), water (300 mL), then 10% aqueous NaCl (300 mL). The resulting solution in ethyl acetate was concentrated, and the solvent switched to isopropyl acetate under reduced pressure. The resulting slurry was filtered, and the wet cake washed with 1:5 isopropyl acetate/heptane (100 mL) and heptane (2×100 mL). The solid (2) was obtained after drying under reduced pressure with a N$_2$ sweep (91%).

Alternative C In a 500 mL round bottom flask, 2,6-dichloro-9H-purine (1) (20 g, 106 mmol) and dry Amberlyst 15H form (1.0 g) was slurried in ethyl acetate (200 mL). 3,4-Dihydro-2H-pyran (17.8 g, 212 mmol) was added and the reaction mixture was stirred at 20-25° C. overnight. The clear solution with resin was filtered and washed with ethyl acetate (40 mL×2). The filtrate was concentrated and solvent switched to heptane at <30° C. The resulting slurry was then filtered, and the solid was washed with heptane (40 mL×2). The wet cake was then dried under reduced pressure. Compound (2) was obtained in 95% isolated yield.

Step 2: Synthesis of Synthesis of 2-Fluoro-9-(tetrahydro-2H-pyran-2-yl)-9H-purin-6-amine (4)

Two alternative preparations for preparing compound (4) were used.

Alternative A In a 1 L vessel equipped with an overhead stirrer and a thermometer, intermediate (2) (75 g, 275 mmol) and potassium fluoride (anhydrous, 80 g, 1373 mmol) were stirred in DMF (750 mL). Trimethylamine (6.49 g, 110 mmol) was charged into the vessel while maintaining the internal temperature between 20-25° C. The vessel was then sealed and stirred for 12-24 hr. At 10° C., aqueous ammonium hydroxide (28 wt %, 53 mL) was charged into the reaction while maintaining the internal temperature below 25° C. The reaction mixture was then transferred to a 3 L RBF equipped with an overhead stirrer. DMF (100 mL) was used to rinse the and the rinse was combined with the main batch for work up. Water (1700 mL) was charged to the combined batch in the 3 L RBF over 3-4 hours, and the resulting mixture was aged at room temperature for 16 hours. A solid was then collected via filtration and washed with 2:1 water/DMF (2×150 mL) followed by water (2×150 mL). Compound (4) (48.2 g; 74% yield) was obtained as a solid after being dried overnight under reduced pressure with a N$_2$ sweep.

Compound (4): $^1$H NMR (500 MHz, DMSO-$d_6$) δ 8.30 (s, 1H), 7.81 (brs, 2H), 5.51 (dd, J=11.0, 2.1 Hz, 1H), 3.98 (m, 1H), 3.67 (m, 1H), 2.21 (m, 1H), 1.93 (m, 2H), 1.70 (m, 1H), 1.57 (m, 2H). $^{19}$F NMR (471 MHz, DMSO-$d_6$) δ−52.16. $^{13}$C NMR (126 MHz, DMSO-$d_6$) δ 159.53 (d, J=203.9 Hz), 158.11 (d, J=21.3 Hz), 150.77 (d, J=19.8 Hz), 139.70 (d, J=2.6 Hz), 117.53 (d, J=4.1 Hz), 81.44, 68.10, 30.33, 24.95, 22.83.

Alternative B Into a 1 L jacketed vessel was charged compound (2) (25 g, 92 mmol), tetramethylammonium chloride (1.00 g, 9.15 mmol), 18-Crown-6 (2.42 g, 9.15 mmol), cesium fluoride (41.7 g, 275 mmol) followed by acetonitrile (250 mL). The slurry was heated at 60° C. for 3 days and then cooled to rt. Aqueous NH$_4$OH solution (28 wt %, 19.1 mL, 275 mmol) was diluted into 500 mL water and the resulting solution was charged into the reaction mixture. The resulting slurry was aged overnight and filtered. The solid was collected via filtration and rinsed with water three times. After drying, compound (4) was obtained with 51% isolated yield.

Alternative C In this alternative the high surface area potassium fluoride resulting from the Preparative Example (2.5 equivalents) above was used. In a 100 mL vessel equipped with an overhead stirrer and a thermometer, intermediate (2) (2.5 g, 9.2 mmol) and high surface area potassium fluoride (anhydrous, 1.3 g, 23 mmol) were stirred in DMF (25 mL). Trimethylamine (0.27 g. 4.6 mmol) was charged into the vessel while maintaining the internal temperature between 20-25° C. The vessel was then sealed and stirred for 12-24 hr. At 10° C., aqueous ammonium hydroxide (28 wt %, 1.8 mL) was charged into the reaction while maintaining the internal temperature below 25° C. Water (42 mL) was charged and the resulting mixture was aged at room temperature for 16 hours. A solid was then collected via filtration and washed with 2:1 water/DMF (1×5 mL) followed by water (4×10 mL). Compound 4 (1.6 g; 70% yield) was obtained as a white solid after being dried overnight under reduced pressure with a N$_2$ sweep.

Alternative D In this alternative potassium fluoride was used in the presence of 18-Crown-6-ether. In a 100 mL vessel equipped with an overhead stirrer and a thermometer, intermediate (2) (2.5 g, 9.2 mmol), 18-Crown-6 ether (1.2 g, 4.6 mmol) and potassium fluoride (anhydrous, 2.7 g. 46 mmol) were stirred in DMF (25 mL). Trimethylamine (0.27 g, 4.6 mmol) was charged while maintaining the internal temperature between 20-25° C. The vessel was then sealed and stirred for 12-24 hr. At 10° C., aqueous ammonium hydroxide (28 wt %, 1.8 mL) was charged into the reaction while maintaining the internal temperature below 25° C. Water (42 mL) was charged and the resulting mixture was aged at room temperature for 16 hours. The resulting solid was then collected via filtration and washed with 2:1 water/DMF (1×5 mL) followed by water (4×10 mL). Compound 4 (1.2 g; 52% yield) was obtained as a white solid after being dried overnight under reduced pressure with a N2 sweep.

Step 3: Synthesis of 2-Fluoro-9H-purin-6-amine (2-FA)

In a 1 L jacketed vessel equipped with an overhead stirrer and a N$_2$ bubbler, 2-fluoro-9-(tetrahydro-2H-pyran-2-yl)-9H-purin-6-amine (4) (30 g, 94.57 wt %, 120 mmol) was stirred in acetonitrile (600 mL) and water (300 mL). Phosphoric acid (85%, 1.0 mL, 14.6 mmol) was charged into the vessel and the reaction mixture was heated at 50° C. for 24 hours. The slurry was then cooled to room temperature and the solid was collected via filtration. The wet cake was washed with water (3×100 mL) and then dried under reduced pressure with a N$_2$ sweep to provide the title compound as a solid (16.9 g, 92% yield). 2-FA: $^1$H NMR (DMSO-$d_6$, 500 MHz): δ 12.87 (brs, 1H), 8.08 (s, 1H), 7.63 1.42 (s, 2H). $^{19}$F NMR (471 MHz, DMSO-$d_6$) δ−52.91. $^{13}$C NMR (126 MHz, DMSO-$d_6$) δ 159.14 (d, J=201.4 Hz), 157.63, 152.30, 139.92, 117.02.

Example 2

This example provides an alternative preparation of the compound (3).

Step 1: Synthesis of 2-Fluoro-9-(tetrahydro-2H-pyran-2-yl)-9H-purine (8)

In a 1 L round bottom flask, 6-chloro-2-fluoro-9H-purine (25 g, 145 mmol) was slurried in ethyl acetate (500 mL). 3,4-Dihydro-2H-pyran (36.6 g, 435 mmol) was added followed by pTSA (0.499 g, 2.90 mmol). The reaction mixture was stirred at 50° C. for 2.5 hours and then cooled to room temperature. The slurry was filtered and the filtrate was solvent switched to isopropyl acetate and heptane under reduced pressure. The resulting slurry was filtered and the wet cake washed with 1:3 isopropyl acetate/heptane (50 mL) and heptane (2×50 mL). A solid (2) was obtained after drying under reduced pressure with a N$_2$ sweep (88%).

Step 2: Synthesis of 2,6-Difluoro-9-(tetrahydro-2H-pyran-2-yl)-9H-purine (3)

6-Chloro-2-fluoro-9-(tetrahydro-2H-pyran-2-yl)-9H-purine (8) (1.0 g, 3.90 mmol) and cesium fluoride (1.2 g, 7.90 mmol) were stirred in trifluorotoluene (10 mL) at 80° C. for 36 hours. The mixture was then filtered and the filtrate was concentrated to provide (3) as an oil.

Compound (3): $^1$H NMR (500 MHz, CDCl$_3$): δ 8.29 (s, 1H), 5.71 (dd, J=10.8, 2.4 Hz, 1H), 4.17 (m, 1H), 3.77 (m, 1H), 2.16 (m, 1H), 2.08 (m, 1H), 2.01 (m, 1H), 1.78 (m, 2H), 1.68 (m, 1H). $^{19}$F NMR (471 MHz, CDCl$_3$) δ−49.11, −65.90. $^{13}$C NMR (126 MHz, CDCl$_3$) δ 160.62 (dd, J=18.3, 265.0 Hz), 157.08 (dd, J=16.8, 219.7 Hz), 156.04 (dd, J=11.6, 17.4 Hz), 143.49, 118.57 (d, J=5.9 Hz), 118.35 (d, J=5.8 Hz), 82.70, 68.92, 31.72, 24.68, 22.51.

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

What is claimed:
1. A process of preparing compound (4),

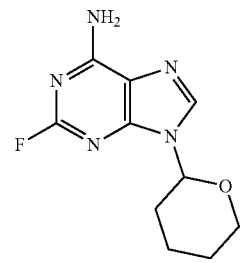

comprising:

(a) treating compound (2)

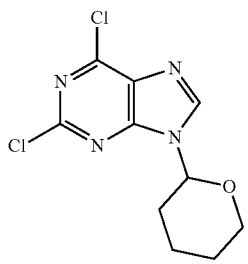
(2)

with a substituted amine reagent and a fluoride salt to provide compound (3), wherein the substituted amine reagent is trimethylamine; and

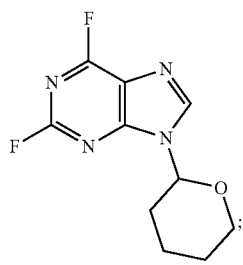
(3)

(b) treating compound (3) with an ammonia reagent to provide compound (4).

2. The process of claim 1, wherein the fluoride salt in step (a) is an alkali metal fluoride or a $C_1$-$C_4$ trialkylammonium fluoride.

3. The process of claim 2, wherein the fluoride salt is potassium fluoride.

4. The process of claim 3, wherein the potassium fluoride has a surface area of at least 0.4 m²/g.

5. The process of claim 1, wherein the treating in step (a) is conducted in a dipolar aprotic solvent.

6. The process of claim 1, wherein the ammonia reagent in step (b) is ammonia, aqueous ammonia, ammonia dissolved in an organic solvent, ammonium acetate, or ammonium carbonate.

7. The process of claim 1, wherein steps (a) and (b) are conducted in a single vessel.

8. The process of claim 1, wherein compound (2) is obtained by reacting compound (1)

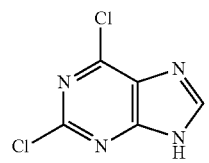
(1)

with dihydropyran in the presence of an acid.

9. A process of preparing 2-fluoroadenine

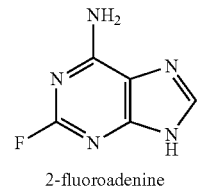
2-fluoroadenine comprising:

(a) treating compound (2)

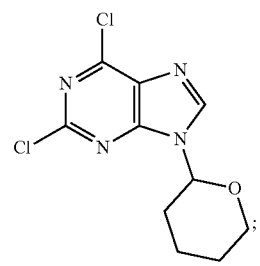
(2)

with a substituted amine reagent and a fluoride salt to provide compound (3)

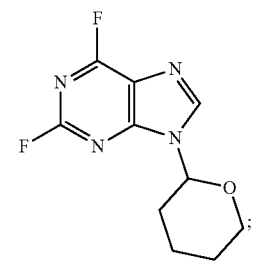
(3)

(b) treating compound (3) with an ammonia reagent to provide compound (4)

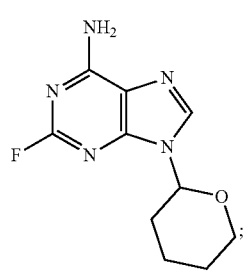
(4)

and (c) treating compound (4) with an acid to provide 2-fluoroadenine.

10. A process for the preparation of 4'-ethynyl-2-fluoro-2'-deoxyadenosine (EFdA)
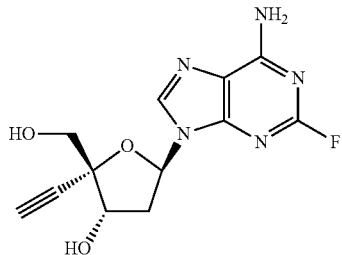
(a) treating compound (2)
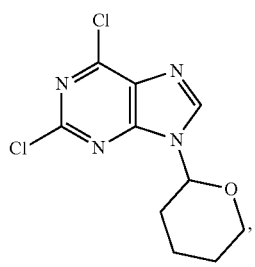
with a substituted amine reagent and a fluoride salt to provide compound (3);
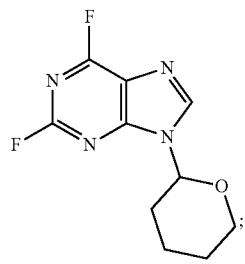
(b) treating compound (3) with an ammonia reagent to provide compound (4)
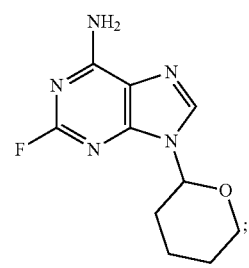
and
(c) converting compound (4) to EFdA.
* * * * *